United States Patent [19]
Terwilliger

[11] Patent Number: 5,188,118
[45] Date of Patent: Feb. 23, 1993

[54] AUTOMATIC BIOPSY INSTRUMENT WITH INDEPENDENTLY ACTUATED STYLET AND CANNULA

[76] Inventor: Richard A. Terwilliger, 1489 Casa Vallencita, Alamo, Calif. 94507

[21] Appl. No.: 690,628

[22] Filed: Apr. 24, 1991

Related U.S. Application Data

[63] Continuation-in-part of Ser. No. 610,006, Nov. 7, 1990.

[51] Int. Cl.⁵ .............................................. A61B 10/00
[52] U.S. Cl. ...................................... 128/753; 128/754; 606/170
[58] Field of Search ............... 128/754, 753, 752, 749, 128/750, 751, 755; 606/167, 170, 171, 184, 185

[56] References Cited

U.S. PATENT DOCUMENTS

| | | | |
|---|---|---|---|
| 4,476,864 | 10/1984 | Tezel | 128/754 |
| 4,570,632 | 2/1986 | Woods | 128/751 |
| 4,600,014 | 7/1986 | Beraha | 128/754 |
| 4,699,154 | 10/1987 | Lindgren | 128/754 |
| 4,747,414 | 5/1988 | Brossel | 128/754 |
| 4,924,878 | 5/1990 | Nottke | 128/751 |
| 4,958,625 | 7/1990 | Bates et al. | 128/754 |

FOREIGN PATENT DOCUMENTS 10321  4/1980  European Pat. Off. ............ 128/754

Primary Examiner—Max Hindenburg
Assistant Examiner—Guy V. Tucker
Attorney, Agent, or Firm—Fliesler, Dubb, Meyer & Lovejoy

[57] ABSTRACT

An automatic biopsy instrument includes a cannula 13 provided over a stylet 11. The stylet 11 directs the cannula 13 to a biopsy site. The instrument urges the cannula 13 past the stylet 11 in order to collect a tissue sample. The stylet 11 initially travels in a direction opposite to the direction of travel of the cannula 13, then travels in the direction of travel of cannula 13 in order to assist firstly in collecting a sample and secondly to assist in severing the tissue sample from the surrounding mass.

18 Claims, 6 Drawing Sheets

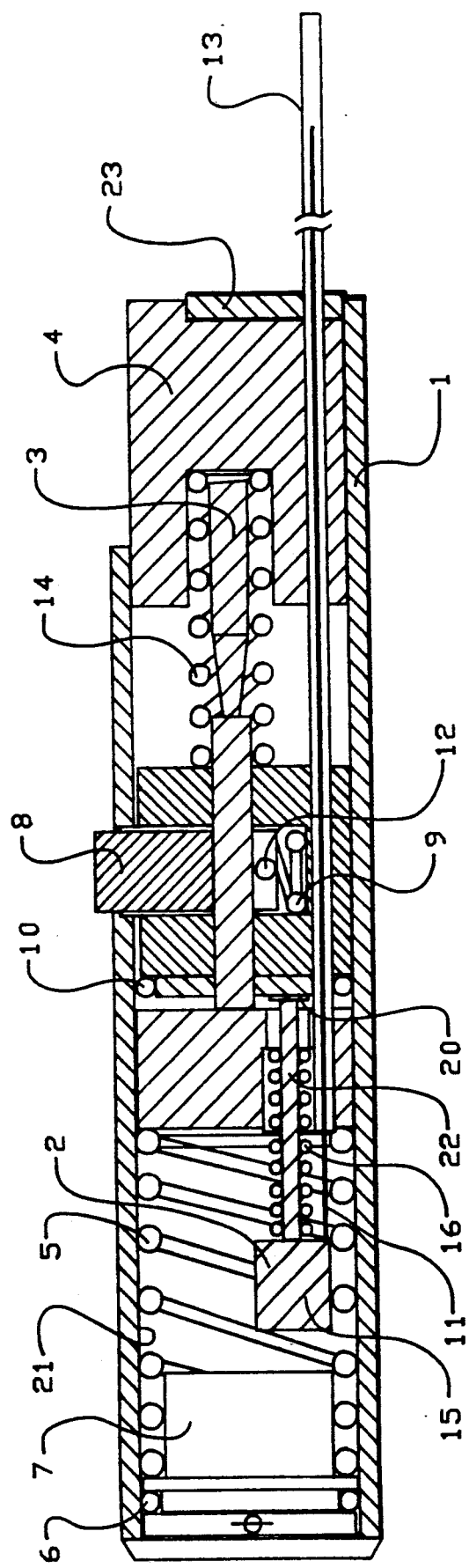
FIG.—1a

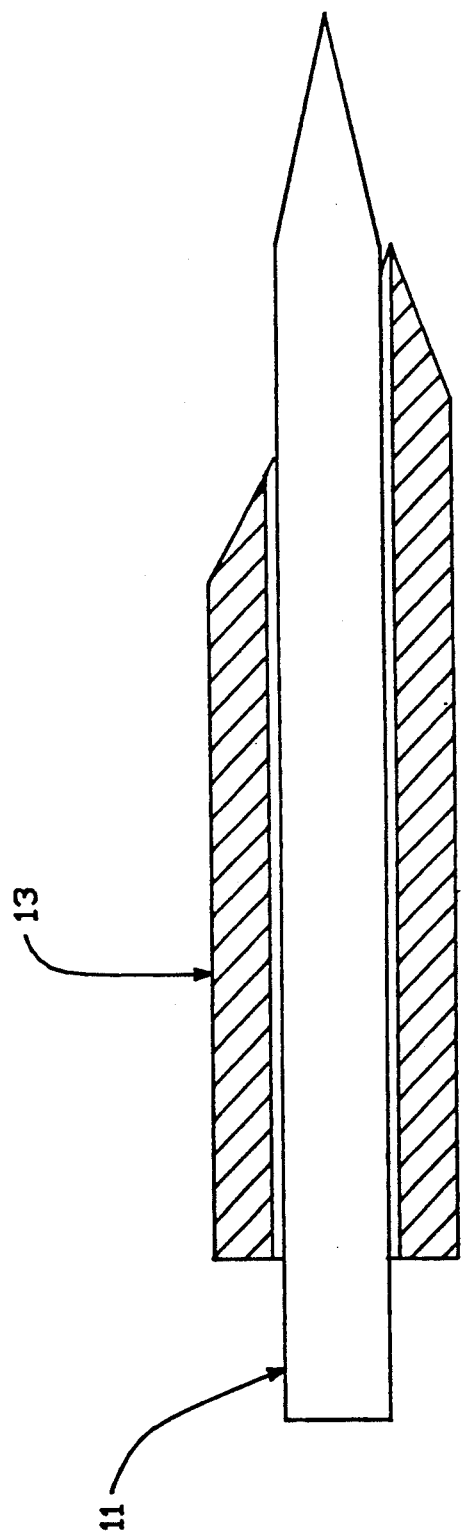
FIG.−2

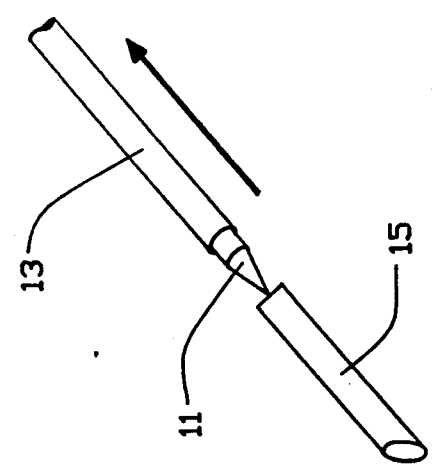
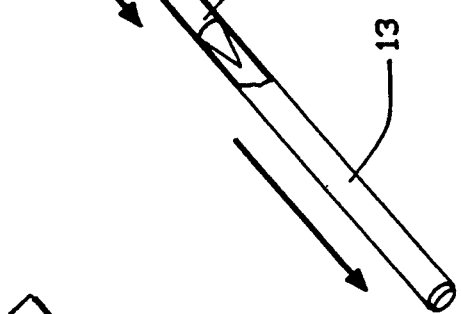
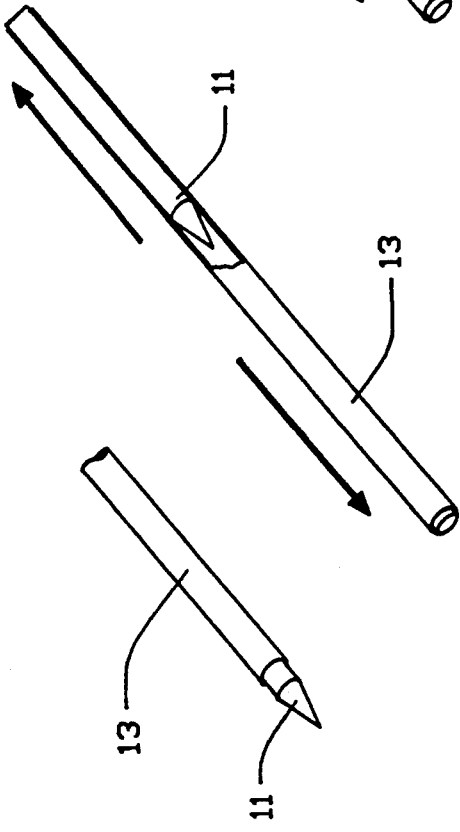

AUTOMATIC BIOPSY INSTRUMENT WITH INDEPENDENTLY ACTUATED STYLET AND CANNULA

CROSS-REFERENCE TO RELATED APPLICATION

The present application is a continuation-in-part of U.S. patent application entitled "AUTOMATIC BIOPSY INSTRUMENT", filed on Nov. 7, 1990, and given U.S. patent application Ser. No. 07/610,006, pending.

FIELD OF THE INVENTION

This invention relates to an automated mechanism for collecting a tissue sample from humans or animals by a procedure referred to as tissue biopsy, and more particularly to an instrument for automatically performing the tissue extraction from a tissue mass in a precise and rapid manner with minimum patient discomfort.

BACKGROUND OF THE INVENTION

It is often desirable and frequently absolutely necessary to sample or test a portion of tissue from humans and even animals to aid in the diagnosis and treatment of patients with cancerous tumors, pre-malignant conditions and other diseases or disorders. Tumors are first noted in a patient by one of three ways. These ways include palpation, X-ray imaging or ultrasound imaging. Typically, in the case of cancer or the suspicion of malignant tumors, a very important process called tissue biopsy is performed to establish whether cells are cancerous.

Biopsy may be done by an open or closed technique. Open biopsy removes the entire tissue mass or a part of the tissue mass. Closed biopsy on the other hand is usually performed with a needle-like instrument and may be either an aspiration biopsy (hollow needle on a syringe) or a cored biopsy (special tissue cutting needle design). In needle aspiration biopsy, individual cells or clusters of cells are obtained for cytologic examination. In core biopsy, a segment of tissue is obtained for histologic examination which may be done as a frozen section or paraffin section.

The methods and procedures of obtaining tissue samples for cytologic or histologic examination have been performed historically by manual insertion and manipulation of the needle. These procedures are performed blind by the physician and guided by feel and known anatomic landmarks.

One prior art manual biopsy device includes a syringe arrangement including a stylet surrounded by a cannula. The stylet has a pointed tip and behind the tip a reduced diameter shank. The diameter of the pointed tip is slightly less than the internal diameter of the cannula such that the tip prevents tissue from entering the cannula as the cannula is passed through surrounding tissue to the point of intended biopsy. An O-ring is placed in sealing relationship between the reduced diameter shank and the internal diameter of the cannula. During operation of the biopsy syringe, the cannula is urged forward past the tip of the stylet in order to collect a tissue sample. As this occurs, a vacuum is formed in the cannula between the O-ring and the tissue sample. This vacuum tends to draw the tissue sample into the cannula.

This device, however, has disadvantages in that it is manual and thus does not give totally reliable results, as discussed below, in taking a biopsy of a very small tumor.

Examples of tissue harvesting devices have been described in U.S. Pat. Nos. 4,651,752; 4,702,260; and 4,243,048.

Two very important innovations in medical technology have influenced the field of tissue biopsy in the last five years. One is the use of tissue imaging devices which allow the physician to see inside the body and visually guide the needle to the tumor mass. The second is the invention of the Automatic Core Biopsy Device (ACBD). The ACBD is an instrument which propels a needle set with considerable force and speed in order to pierce the tumor mass and collect the tissue sample. This ACBD has allowed physicians to test tissue masses in the early stages of growth and has contributed to the medical trend of early diagnosis and successful treatment of cancer.

The Automated Core Biopsy Device allows a biopsy to be performed on tumor masses as small as two millimeters in diameter. This procedure is performed under ultrasound or X-ray guidance. Tumors of this size cannot be biopsied reliably by hand since the tumor is about the same size as the biopsy needle. Manual attempts at biopsy pushes the tumor away without piercing the mass. Automatic puncture devices accelerate the needle at such a velocity that even a small tumor can be pierced.

Automated Core Biopsy Devices (ACBD) use the True Cut needle set design. The True Cut needle is comprised of an inner notched stylet 17 (FIG. 5a) with an outer cannula 16 (FIG. 5a). The stylet is advanced into the tissue under spring power followed by the cannula which cuts and traps the tissue sample 18 (FIGS. 5a, 6) in the notch of the stylet. The True Cut needle yields a core tissue sample 18 which is semi-circular in cross-section with a length determined by the stroke of the ACBD.

The stylet is a needle with a notched cut-out at the distal end. The cannula is a hollow needle with an angled cutting surface at the distal end which slides over the stylet. When the stylet is pushed into the tissue, the tissue is pierced and relaxes into the notched cut-out. When the cannula is slid forward, the tissue in the notch of the stylet is sliced off and retained in the notch until the cannula is drawn back.

The most common True Cut needle size used by ACBD's is 18 gage. The use of 18 gage needles is a compromise between the physician's desire to use the smallest, least invasive, needle gage and the pathologist's needs for as large a tissue sample as possible to minimize false-positive diagnosis. This compromise in needle size leads the physician to obtain multiple core samples from the biopsy site to allow the pathologist sufficient tissue for an accurate diagnosis.

The requirements of the physician and the pathologist dictate the need for an alternative approach in the function and design of the conventional ACBD and needle sets. The ideal product would allow the use of smaller needle gages and/or lessen the need for multiple samples to be taken from a given biopsy site.

SUMMARY OF THE INVENTION

Based on the prior art instruments for biopsy sampling of tissue masses and the actual present state of this art, there exists a need for an instrument which is capable of obtaining biopsy samples which yield more tissue volume for a given needle gage than currently marketed devices. This increased tissue volume allows the physician to use smaller needle gages and/or reduce the number of punctures per biopsy site.

The ability to use smaller needle gages and/or less punctures per biopsy site, opens up the other major areas of biopsy procedures to the use of a device which will increase the reliability and safety of these procedures.

Accordingly, I have invented an instrument for removing cylindrically shaped tissue samples of pre-determined size from a tissue mass with an instrument that automatically penetrates, captures and removes the tissue sample for examination.

The instrument is a spring powered mechanical design. The needle set is integral with the housing and consists of a outer hollow cannula and an inner pointed tipped stylet. The stylet and the cannula are driven forward under spring force in a defined motion in relation to each other.

In a preferred form, the housing is comprised of a hollow tube which guides a spring backed piston to which the cannula and stylet are attached. The piston is pushed backwards in a chamber described by this housing by means of an outer actuator which compresses the main spring. A locking means holds the piston and main spring in the compressed state in which the inner stylet is positioned inside the cannula and protrudes out of the distal end of said cannula. Once the spring is released, the piston and cannula are driven forward. As the piston and cannula advance, the stylet is held stationary relative to the housing by a secondary spring on the far side of the piston until a stop is reached, at which point the stylet tracks the forward motion of the advancing cannula for the rest of the movement of the cannula.

At the end of the forward motion of the cannula, the piston comes to rest against a block which incorporates an "O" ring seal. The chamber in which the piston moves is sealed at the distal end of the device by an end cap with integral seal and at the proximal end by a block with the integral seal. At the end of the forward motion of the piston, the chamber is sealed by the spring loaded position of the piston against said block, allowing only the hollow bore of the cannula as an exit.

As the spring is released, tissue is penetrated by the forward motion of the cannula, the tissue advances up into the hollow bore of the cannula created by the relative motion of the cannula to the stylet. With the inner stylet remaining stationary, the cannula advances a defined distance into the tissue, at which point the inner stylet begins to follow the cannula, stopping the relative motion of the stylet with respect to the cannula. Since the cannula continues the forward motion and the hollow bore is filled with pierced tissue backed up against the stylet, the further advancement of the cannula slices off the captured tissue trapped inside of the cannula from the surrounding tissue at the distal end of the cannula. Essentially, the present design ensures that no matter if a soft or a firm tissue sample is being taken, the inventive device reliably slices off the tissue sample so that the tissue sample is not left in the patient when the cannula is removed.

With the tissue sliced off at the tip of the distal end of the cannula and the piston sealed against the inner "O" ring seal of the block, the captured tissue remains positioned in the hollow bore of the cannula as the needle is withdrawn from the surrounding tissue. The captured tissue acts as the final seal of the chamber created by the housing and the associated internal parts ensuring that the tissue sample is held in the cannula as the cannula is withdrawn from the patient.

The stylet is a pointed needle positioned inside the cannula. At the distal end of the stylet, a pointed tip facilitates the introduction of the needles into the tissue mass. The stylet is positioned flush to the end of the cannula in the cocked positioned. In the cooked position, the stylet prevents tissue from entering the cannula as the needle set is introduced into the body. As the device is fired, the cannula advances while the stylet remains stationary, thus allowing space for the penetrated tissue to enter the cannula.

As the device is cooked and the piston and cannula are retracted, the cannula is moved backwards over the stylet, pushing the tissue sample out of the cannula. This action removes the tissue sample and cocks the device in one motion.

A volumetric analysis of a cross-section of tissue area collected with the True Cut needle set vs. the cylindrical core samples of this invention follows:

| Stylet | Gage | X-Section Area | Percentage |
|---|---|---|---|
| True Cut | 18 ga. | .0007 sq/in. | |
| Cylindrical | 18 ga. | .0012 sq/in. | 72% larger sample |
| Cylindrical | 20 ga. | .0005 sq/in. | 71% of True Cut 18 ga. |

For a given needle gage and core length, the cylindrical core volume of this invention is 72% larger than that provided by the True Cut needle set. A 20 gage cylindrical needle in accordance with this invention will yield 71% of the tissue yielded by an 18 gage True Cut needle set.

Accordingly, it is a principle object of this invention to provide an automated tissue sampling device for obtaining tissue samples which have a circular cross-section. Such a cross-section provides for more tissue mass for a given needle gage, provides for a less invasive procedure with reduced tissue trauma and allows for the maximum tissue to be harvested with the minimum number of samples taken.

It is a further object of this invention to provide a biopsy instrument which accelerates a needle at such a velocity so as to allow penetration of small tissue masses that would otherwise be too small for a closed biopsy procedure.

It is another object of this invention to provide an instrument which may be used to obtain multiple tissue samples from the same biopsy site without disassembling the device or actuating multiple mechanisms or controls.

It is yet another object of the invention to provide an automated biopsy device which creates a seal in an inner chamber substantial enough to effectively assist in holding the tissue in the cannula as the cannula is withdrawn.

These and other objects of the invention will be apparent from the following descriptions and claims.

BRIEF DESCRIPTION OF THE DRAWINGS

The above noted advantages and other characteristic features of the present invention will be apparent from the accompanying drawings, and pointed out in the following detailed description of the preferred embodiment of the invention in which references will be made to the accompanying drawings wherein like reference numerals designate corresponding parts and wherein:

FIGS. 1a, 1b and 1c are cross-sectional side elevation views of the biopsy instrument of the invention. FIG. 1a depicts the device in the "fired" position, FIG. 1b depicts the device in the process of being "cooked" with the thumb knob pushed rearwardly and FIG. 1c depicts the device in the "cocked" position;

FIG. 2 is a partial side elevation of the needle at its distal end;

FIGS. 3a, 3b, 3c and 3d are pictorial illustrations of needle positions in various stages of the operation of an embodiment of the invention;

DESCRIPTION OF THE PREFERRED EMBODIMENT

Figure 1B:
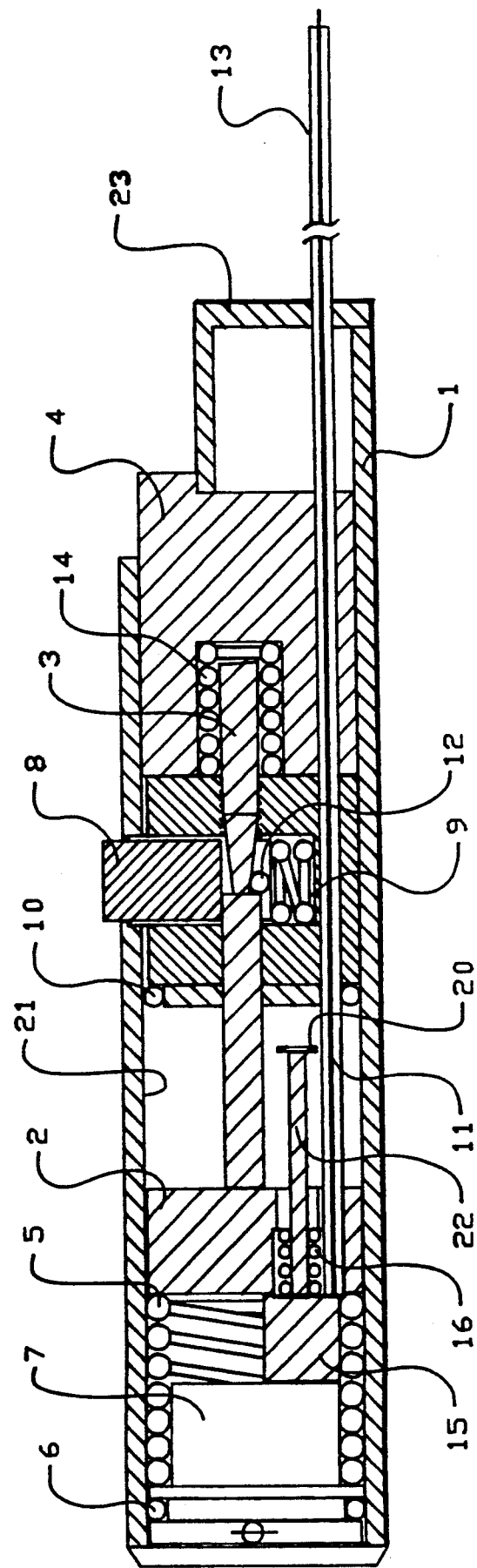

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1C:
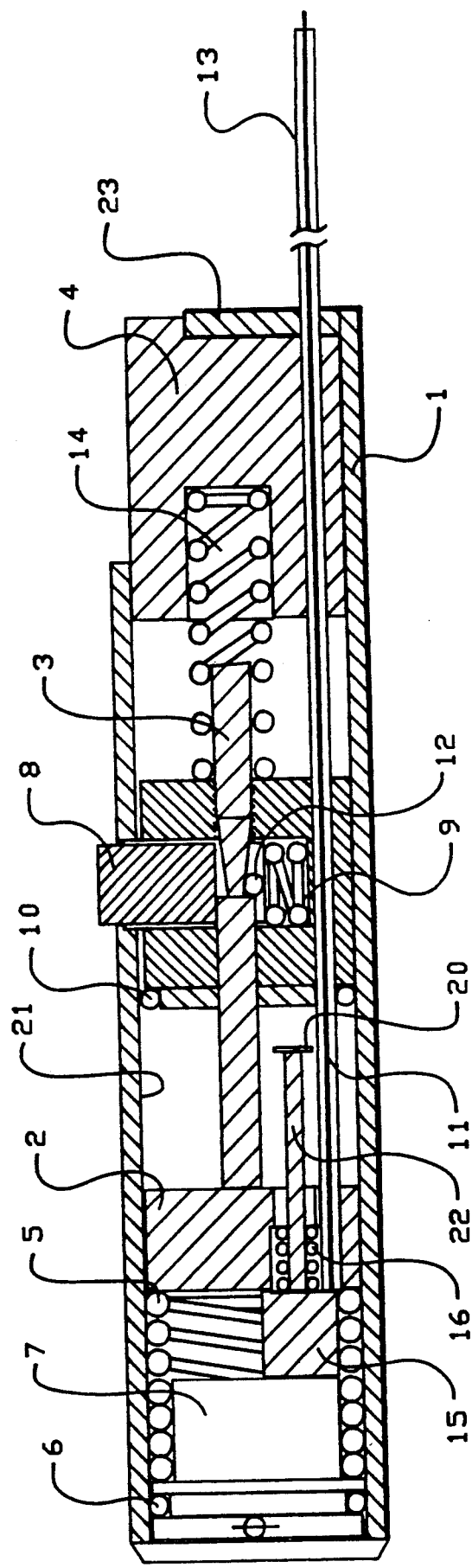

Considering now the drawings in detail, FIG. 1a illustrates a side elevation view of the embodiment of the inventive biopsy instrument which is shown to depict the main components of said embodiment with the main body or housing is shown generally at 1 and the tissue piercing and removal means shown by stylet 11 and cannula 13. The main housing means extends from end cap 7 to the distal end of thumb knob 4. Within said housing 1 is a plunger block 2. Plunger rod 3 is depressed by exerting pressure on thumb knob 4 which compresses the main spring 5. Plunger 2 and main spring 5 are held in the compressed state by latch pin 12 which resides in actuator button 8. Spring 9 pushes actuator button 8 and latch pin 12 up against plunger rod 3. As plunger rod 3 is depressed, latch pin 12 slides along plunger rod 3 until latch pin 12 detents into the annular groove in plunger rod 3 (FIG. 1b). Latch pin 12 holds plunger rod 3 in place and thus holds plunger 2 and main spring 5 in compression until such time that actuator button 8 is depressed. Once the biopsy instrument is cocked, the spring 14 returns thumb knob 4 to an initial position against stop 23 of the main body 1 (FIG. 1c).

When the actuator button 8 is depressed, plunger rod 3 is released and main spring 5 pushes plunger 2 forward with the associated component cannula 13 which is attached to plunger 2. Cannula 13 is fixed to plunger 2 through a hole in plunger 2. Cannula 13 is sealed in the hole and communicates with an inner chamber 21 defined by the inside of housing 1. Plunger 2 when in contact with "O" ring seal 10, and end cap 7 with associated "O" ring seal 6, create an air tight inner chamber 21 of main housing 1 with the hollow body of cannula 13 the only avenue of air passage. Depressing actuator button 8 releases plunger rod 3 thus allowing plunger 2 to be forced forward by main spring 5. As plunger 2 moves forward, spring 16 pushes rearwardly against stylet plunger block 15 thereby holding stylet 11 stationary relative to the housing and causing a relative movement of the cannula 13 and stylet 11, such that the tip of cannula 13 extends out beyond the tip of stylet 11.

Cannula 13 continues forward motion as stylet 11 remains stationary. The associated relationship of motion between cannula 13 and stylet 11 is maintained until the stop collar 20 of plunger 22 contacts the plunger block 2. At this point, plunger 2 forces the stop collar 20 to move forward, thereby causing the stylet 11 to move forward with cannula 13. Both cannula 13 and stylet 11 move forward through the surrounding tissue, cutting off the captured tissue in cannula 13, until the plunger block 2 comes to rest against "O" ring 10, sealing the chamber 21 of the main housing 1. The captured tissue in cannula 13 acts as a seal to the chamber 21 created in the main housing 1 and allows the withdrawal of the needles from the surrounding tissue without accidental loss of the captured tissue.

FIG. 2 illustrates a cross-sectional side elevation view of the distal ends of cannula 13 and stylet 11. Stylet 11 is a solid rod with a pointed tip at the distal end. Stylet 11 prevents tissue from entering cannula 13 as it is passed through the surrounding tissue to the point of intended biopsy.

FIGS. 3a through 3d illustrate the preferred embodiment of the distal needle end of this invention. Four stages of motion are depicted.

FIG. 3a shows the preferred embodiment of cannula 13 and stylet 11 in the "cocked" position.

FIG. 3b shows the preferred embodiment of cannula 13 and stylet 11 in the act of being "fired".

FIG. 3c shows the continuation of motion of cannula 13 with the reversal of motion of the stylet 11.

FIG. 3d shows the preferred embodiment of cannula 13 and stylet 11 in the act of "cocking" the mechanism and the subsequent expulsion of the tissue sample 15.

Figure 4A:
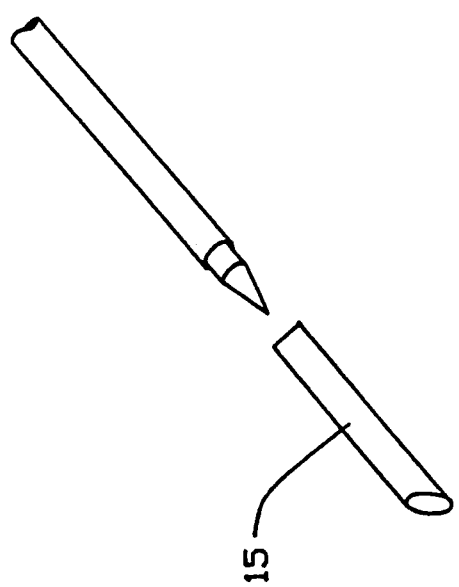
FIG. 4a is a pictorial illustration of the preferred embodiment of the distal needle end of the invention.

FIG. 4a illustrates the preferred embodiment of the distal needle end with the expulsed tissue sample 15.

Figure 4B:
FIG. 4b is a pictorial illustration of the cross-section of tissue obtained from the preferred embodiment of this invention.

FIG. 4b illustrates the cross-section of tissue 15 obtained from the distal needle end of the preferred embodiment of this invention.

Figure 5A:
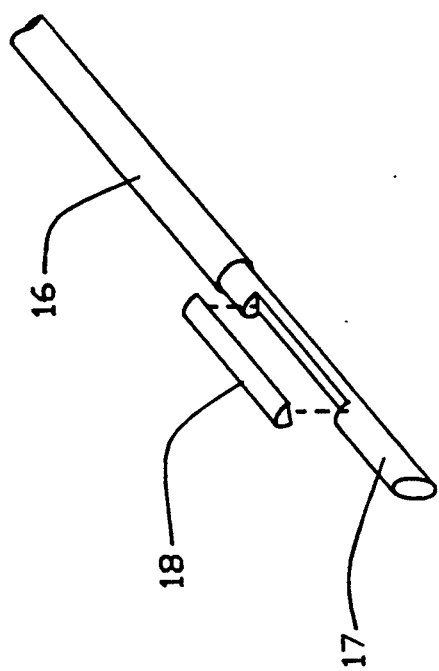
FIG. 5a is a pictorial illustration of the distal needle end of the prior art.

FIG. 5a illustrates the distal needle end of the prior art device with the expulsed tissue sample 18.

Figure 5B:
FIG. 5b is a pictorial illustration of the cross-section of tissue obtained from the prior art.

FIG. 5b illustrates the cross-section of tissue 18 obtained from the distal needle end of the prior art device.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

I claim:

1. An automatic biopsy instrument including:
   a body;
   a cavity defined in said body;
   a cannula piston movably mounted in said cavity;
   means for biasing said cannula piston relative to said cavity;
   first means for urging said cannula piston against the biasing means;
   an elongate cannula with an elongate inner bore;

means for securing said cannula to said cannula piston so that the cannula can move with the cannula piston;

an elongate stylet positioned in said inner bore of the cannula; and second means for urging the stylet away from said cannula piston in a direction opposite to the direction of the motion of the cannula as caused by the biasing means so as to allow capture of biopsy tissue in said cannula when said stylet is in a relatively retracted position.

2. The instrument of claim 1 wherein:

said biasing means can bias said cannula piston to an uncocked position;

said first urging means can urge said cannula piston against said biasing means to a cocked position; and means for selectively locking said cannula piston in said cocked position.

3. The instrument of claim 1 including:

said cannula having a distal end;

said stylet having a tip;

wherein said first urging means can urge said cannula piston against said biasing means to a cocked position, such that said tip of said stylet is extended from said distal end of said cannula; and wherein said biasing means can bias said cannula piston to an uncocked position wherein said distal end of said cannula is urged over and past said tip of said stylet.

4. The automatic biopsy instrument of claim 1 wherein:

said second means for urging the stylet includes a stylet piston, means for movably mounting the stylet piston to the cannula piston, and means for biasing the stylet piston with respect to the cannula piston; and means for securing the stylet to the stylet piston.

5. The automatic biopsy instrument of claim 4 wherein:

said means for movably mounting the stylet piston to the cannula piston includes a passage defined in the cannula piston;

said stylet piston including means for retaining said stylet piston in said passage while allowing limited relative motion between the stylet piston and the cannula piston, said retaining means including first and second retaining ends; and said means for biasing the stylet piston with respect to the cannula piston located between the cannula piston and one of the first and second retaining ends.

6. The automatic biopsy instrument of claim 1 including:

said inner bore of the cannula communicating with the cavity; and means for creating a seal between the cannula piston and the cavity with the cannula piston biased against said cavity by the biasing means in order to ensure that the tissue sample is retained in the cannula.

7. An automatic biopsy instrument including:

a body;

a cannula extending from said body, which cannula defines an inner bore;

a cannula piston moveably mounted in said body;

means for securing the cannula to the cannula piston;

a stylet positioned in said inner bore of said cannula;

first means for urging said cannula in a first direction past said stylet in a rapid manner in order to collect a tissue sample in said inner bore of said cannula; and second means for urging said stylet away from said cannula piston in a second direction which is opposite to the first direction so as to allow capture of biopsy tissue in said cannula when said stylet is in a relatively retracted position.

8. The automatic biopsy instrument of claim 7 wherein:

said body defines an internal cavity;

said first urging means includes a cannula piston movably mounted in the cavity and a means for biasing the cannula piston in said first direction.

9. The automatic biopsy instrument of claim 8 wherein:

said second urging means includes a stylet piston, means for movably mounting the stylet piston to the cannula piston, and means for biasing the stylet piston with respect to the cannula piston; and means for securing the stylet to the stylet piston.

10. The automatic biopsy instrument of claim 9 wherein:

said means for movably mounting the stylet piston to the cannula piston includes a passage defined in the cannula piston;

said stylet piston including means for retaining said stylet piston in said passage while allowing limited relative motion between the stylet piston and the cannula piston, said retaining means including first and second retaining ends;

said means for biasing the stylet piston with respect to the cannula piston located between the cannula piston and one of the first and second retaining ends.

11. The automatic biopsy instrument of claim 8 including:

said inner bore of the cannula communicating with the internal cavity; and means for creating a seal between the cannula piston and the internal cavity with the cannula piston biased in the first direction by said first urging means in order to ensure that the tissue sample is retained in the cannula.

12. The automatic biopsy instrument of claim 7 including:

said second means for subsequently allowing the stylet to move in the first direction with the cannula, in order to allow capture of biopsy tissue.

13. An automatic biopsy instrument including:

a body;

a cannula extending from said body, which cannula defines an inner bore;

a stylet positioned in said inner bore of said cannula;

first urging means including a cannula piston attached to said cannula for moving said cannula in a first direction relative to said stylet in a rapid manner in order to collect a tissue sample in said inner bore of said cannula; and second urging means for urging said stylet away from said cannula piston in a second direction which is opposed to the first direction, said cannula piston subsequent to initial movement in the first direction, engaging a portion of said second urging means to move said stylet in said first direction with the cannula.

14. The automatic biopsy instrument of claim 13 wherein:
   said second urging means includes a stylet piston, means for movably mounting the stylet piston to the cannula piston, and means for biasing the stylet piston with respect to the cannula piston; and
   means for securing the stylet to the stylet piston.

15. The automatic biopsy instrument of claim 14 wherein:
   said means for movably mounting the stylet piston to the cannula piston includes a passage defined in the cannula piston;
   said stylet piston including means for retaining said stylet piston in said passage while allowing limited relative motion between the stylet piston and the cannula piston, said retaining means including first and second retaining ends;
   said means for biasing the stylet piston with respect to the cannula piston located between the cannula piston and one of the first and second retaining ends.

16. The automatic biopsy instrument of claim 13 including:
   an internal cavity defined by said body;
   said inner bore of the cannula communicating with the internal cavity; and
   means for creating a seal between the cannula piston and the internal cavity with the cannula piston urged in the first direction in order to ensure that the tissue sample is retained in the cannula.

17. An automatic biopsy instrument including:
   a body;
   a cannula extending from said body, which cannula defines an inner bore;
   a stylet positioned in said inner bore of said cannula:
   first urging means including a cannula piston attached to said cannula for extending said cannula from said body in a first direction in order to collect and sever a tissue sample; and
   second urging means including a stylet piston attached to said stylet for biasing said stylet away from said cannula piston in a second direction opposite to the first direction, said cannula piston, subsequent to initial movement in the first direction, engaging a portion of said stylet piston to move said stylet in the first direction of motion of the cannula in order to assist the cannula in severing the tissue sample.

18. A needle set for an automatic biopsy instrument comprising:
   a stylet;
   a hollow cannula;
   said stylet sized in order to be able (1) to fit inside of the hollow stylet, (2) to move relative to the hollow cannula from a position extending from the hollow cannula to a position withdrawn inside of the hollow cannula in order to define a collection space, and (3) to allow vacuum to communicate between the stylet and the cannula to the collection space to assist in the holding of a tissue sample in the collection space;
   means adapted for securing the hollow cannula to a cannula piston of an automatic biopsy instrument; and
   means adapted for securing the stylet to a stylet piston of the automatic biopsy instrument so that under the urging of the automatic biopsy instrument the stylet and cannula can move from (1) a cocked position with the stylet extending from the cannula, (2) to a first intermediate motion with the cannula moving past the stylet in order to define the collection space for capturing tissue, (3) to a second intermediate motion with stylet and the cannula moving together in order to sever captured tissue, (4) to an uncocked position with the cannula at rest and extended past the stylet.

* * * * *